United States Patent [19]
Shannahan

[11] Patent Number: 5,460,601
[45] Date of Patent: Oct. 24, 1995

[54] ELASTIC FOOTWRAP

[76] Inventor: Donald R. Shannahan, 112 W. Logan, Caldwell, Id. 83605

[21] Appl. No.: 27,187

[22] Filed: Mar. 5, 1993

[51] Int. Cl.$^6$ .................................................. A61F 13/00
[52] U.S. Cl. ................... 602/66; 2/16; 602/65; 602/62; 36/91
[58] Field of Search ................. 602/61, 62, 63, 602/64, 65, 66, 23, 30; 2/16, 20, 21, 159, 162; 36/34 R, 93, 94, 11.5, 4, 91

[56] References Cited

U.S. PATENT DOCUMENTS

| | | | |
|---|---|---|---|
| 715,543 | 12/1902 | Bosworth | 602/30 |
| 822,138 | 5/1906 | Little . | |
| 982,664 | 1/1911 | Fischer . | |
| 1,365,512 | 1/1921 | Lewis . | |
| 1,406,583 | 2/1922 | Ruge . | |
| 1,512,218 | 10/1924 | Goldsmith . | |
| 1,772,179 | 9/1930 | Finkelstein | 602/30 |
| 2,237,652 | 4/1941 | Capezio | 36/94 |
| 2,561,836 | 6/1951 | Holm | 602/62 |
| 2,708,930 | 5/1955 | Lowman | 602/27 |
| 3,724,458 | 4/1973 | Piper | 602/62 |
| 4,084,586 | 4/1978 | Hettick | 128/157 |
| 4,085,745 | 4/1978 | Alenares | 128/165 |
| 4,476,858 | 10/1984 | Curtis | 602/62 |
| 4,550,511 | 11/1985 | Gamm | 36/91 |
| 4,597,395 | 7/1986 | Barlow et al. | 602/65 |
| 4,958,384 | 9/1990 | McCrane | 2/20 |
| 5,092,318 | 3/1992 | More et al. | 602/27 |

*Primary Examiner*—Paul B. Prebilic

[57] ABSTRACT

An elastic footwrap for treating plantar fasciitis by relaxing and shortening the musculatures of the foot. The footwrap is made of elastic material having a body and an arch support. Both the body and the arch support are generally rectangular. The body covers the top and bottom of the foot and has an ankle opening and toe openings. The ends of the body are secured at the heel so that a predetermined compressive force is exerted along the bottom of the foot when the footwrap is in operative position on the foot. The arch support is positioned perpendicular to the body. The ends of the arch support are secured on the top of the foot so that the arch support envelopes and supports the arch when the footwrap is in operative position on the foot.

7 Claims, 5 Drawing Sheets

ELASTIC FOOTWRAP

FIELD OF THE INVENTION

The invention relates generally to a device for supporting the foot and more particularly to a device for relaxing and shortening the musculatures of the foot to treat plantar fasciitis.

BACKGROUND OF THE INVENTION

Plantar fasciitis is a common foot disorder that causes heel spur and other types of plantar facial pain. Plantar fasciitis can be treated, and the associated pain relieved, by shortening and relaxing the musculatures of the foot. The various elastic footwraps currently available typically provide only superficial support for the veins of the foot, the arch or the ankle joint. Such footwraps are not designed to nor do they shorten and relax the musculatures of the foot. Accordingly, it is one object of the invention to provide an elastic footwrap that effectively treats plantar fasciitis by shortening and relaxing the musculatures of the foot.

Plantar fasciitis is currently treated by wrapping the foot with tape or materials with tape-like backing. If done correctly, taping the foot can shorten and relax the musculatures of the foot to effectively treat plantar fasciitis and relieve the pain associated therewith. But taping must be done by a physician or other trained medical person and may not be removed and reinstalled by the patient. It is desireable to treat plantar fasciitis with a device that may be correctly used by the patient, including removal and reinstallation, to lower the cost of treatment and to minimize the incidental discomfort and inconvenience associated with taping (such as itching and difficulty bathing). Accordingly, it is another object of this invention to provide a device for treating plantar fasciitis that may be correctly removed and reinstalled by the patient.

Taping treats plantar fasciitis by fixing the foot in a predetermined position. Once the foot is taped, its position may not be adjusted with any significant degree of precision. Some adjustment is possible, but only by re-taping the foot. Re-taping is time consuming and expensive. It is desireable that the device used to treat plantar fasciitis provide a means for accurately adjusting the position of the foot in an efficient and cost effective manner. Accordingly, another object of this invention is to provide a device for treating plantar fasciitis that allows for the adjustment of the position of the foot with a significant degree of precision in a way that is quicker and less costly than taping.

SUMMARY OF THE INVENTION

The above and other objects of the invention are achieved by a footwrap made of elastic material, the footwrap comprising a body and an arch support. The body covers the top and bottom of the foot and has an ankle opening and toe openings. The ankle opening extends from above the heel forward along both sides of the foot just below the protuberance of the ankle to the top of the foot. The toe openings are positioned forward of the ankle opening so that the toes are inserted through the toe openings when the footwrap is placed on the foot. The ends of the body are secured at the heel in such a way that a predetermined compressive force is exerted along the bottom of the foot. The arch support is positioned perpendicular to the body. The ends of the arch support are secured on the top of the foot or along the side of the foot so that the arch support envelopes and supports the arch when the footwrap is placed on the foot.

BRIEF DESCRIPTION OF THE DRAWINGS

These and other features, aspects, and advantages of the invention will become better understood with regard to the following description, claims and accompanying drawings where:

DESCRIPTION

Figure 1:
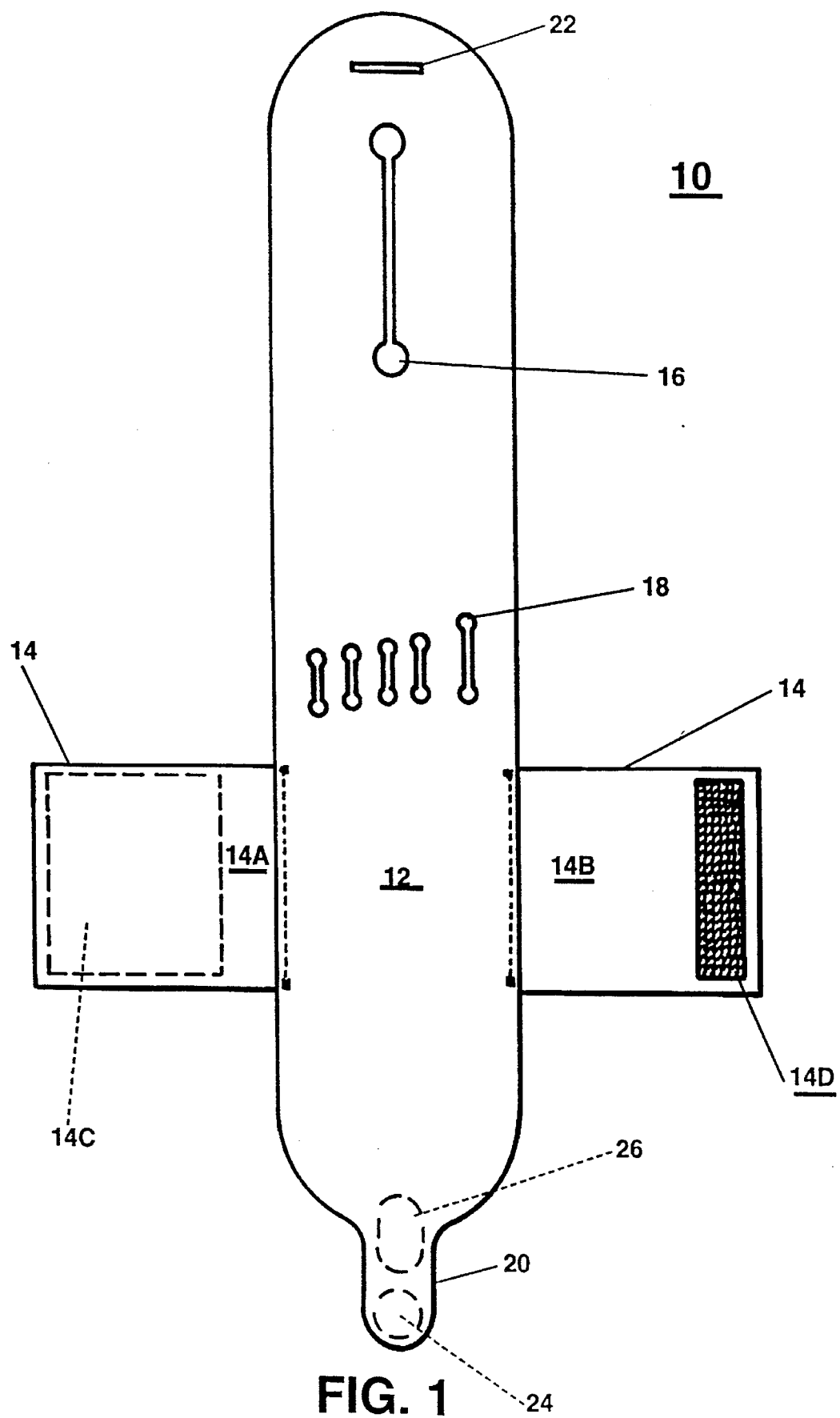
FIG. 1 shows a plan view of one embodiment of the footwrap.
Figure 2A:
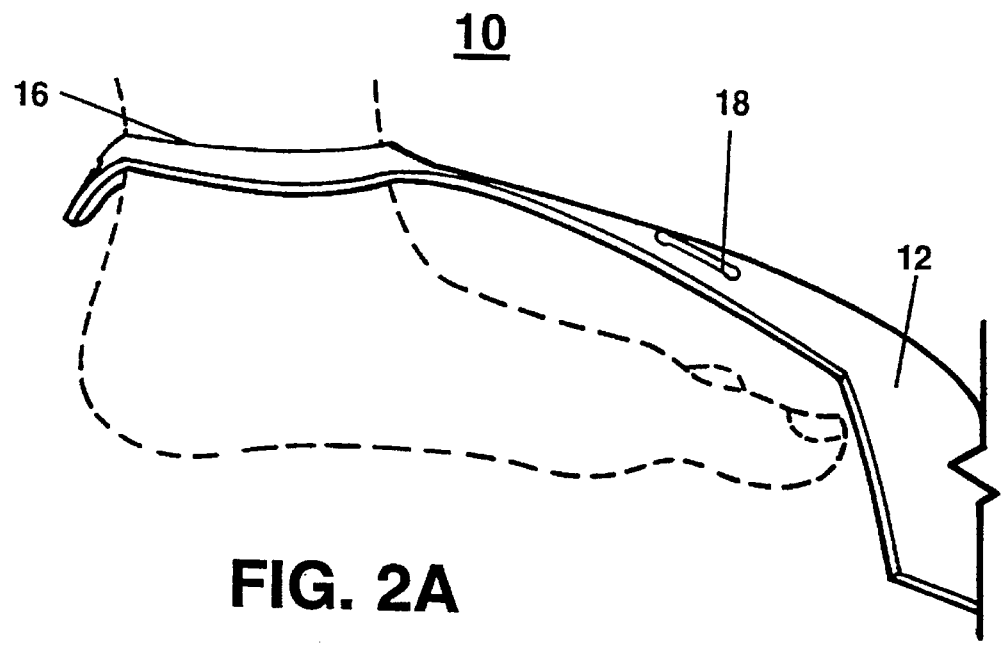
FIGS. 2A and 2B show the footwrap of FIG. 1 sequentially in various positions being installed on the foot.
Figure 2B:
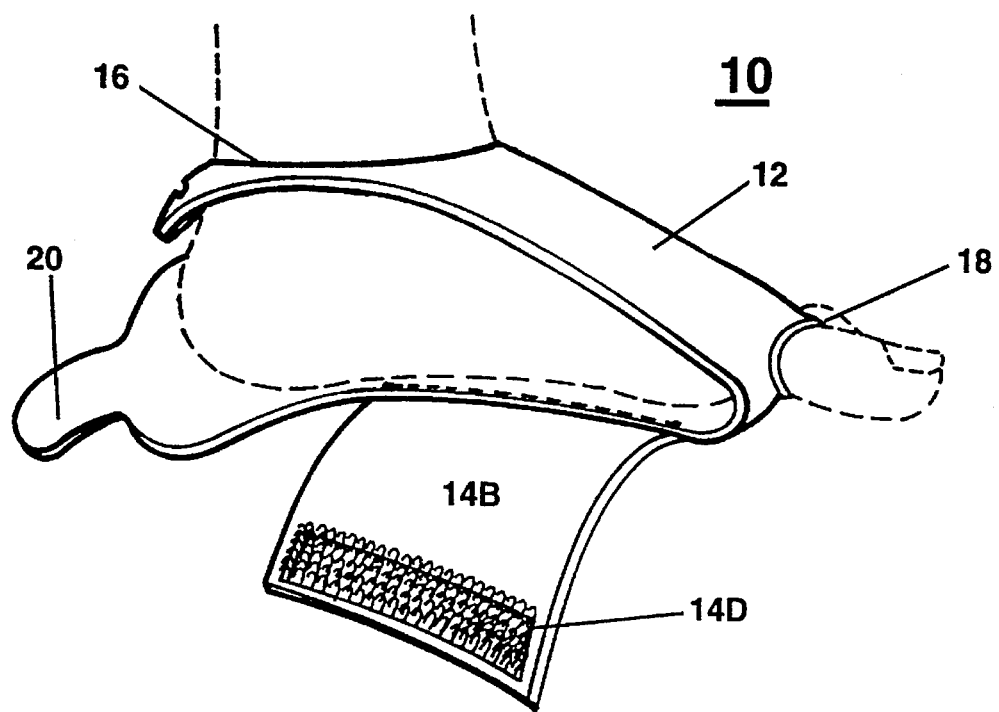
Figure 2C:
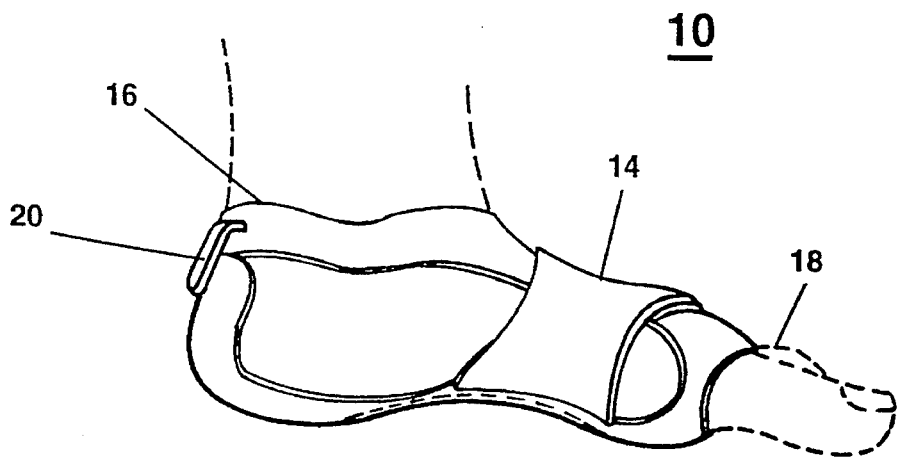
FIG. 2C shows the footwrap of FIG. 1 in operative position on the foot.

The preferred embodiment of the invention, illustrated in plan view in FIG. 1, is a footwrap 10 having a body 12 and an arch support 14. The body 12 is made of elastic material and is generally rectangular, being sized and proportioned to the individual foot. The body 12 has an ankle opening 16 and a plurality of toe openings 18. As illustrated in FIGS. 2A, 2B and 2C, the ankle opening 16 extends from above the heel at the lower part of the Achilles tendon forward along both sides of the foot below the protuberance of the ankle to the top of the foot just below the angle of the ankle. The toe openings 18 are positioned forward of the ankle opening 16 so that the toes may be inserted through the toe openings 18 when the footwrap is installed on the foot.

One end of the body forms a tongue 20 and the other end has a slot 22 therein for receiving the tongue 20 when the footwrap is installed on the foot. A patch 24 is attached to the end of the tongue 20. A complementary patch 26 is attached to the body 12 immediately in front of the tongue 20 to engage patch 24 when the tongue 20 is inserted through the slot 22. Patches 24 and 26 are made of synthetic materials that adhere when pressed together, commonly sold under the trademark "Velcro." The slot 22 is sufficiently wide to allow the tongue 20 to pass through it to secure the ends of the body 12 as shown in FIG. 2C.

Figure 1A:
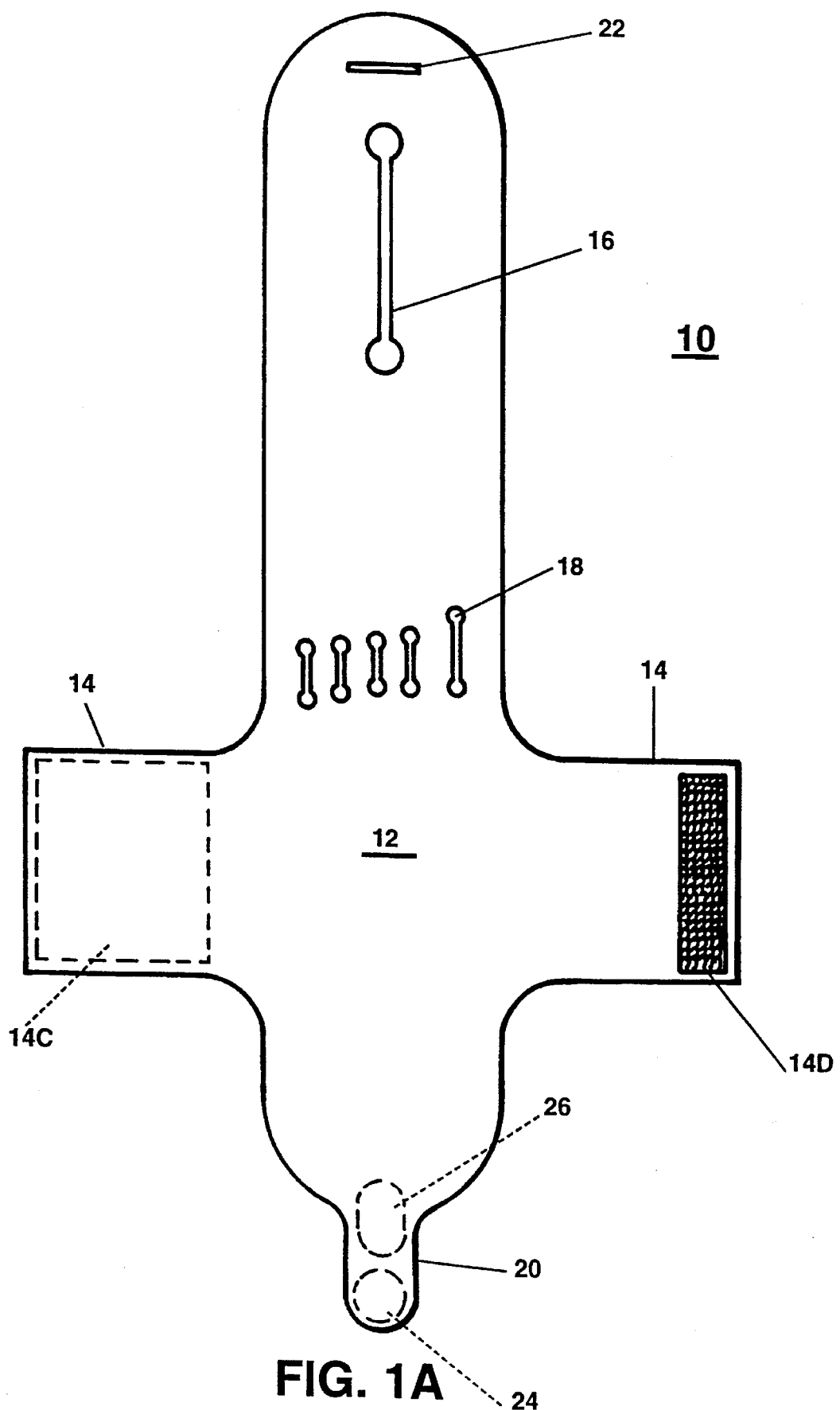
FIG. 1A shows a plan view of another embodiment of the footwrap.

The arch support 14 is made of elastic material and is generally rectangular, having a first end 14A and a second end 14B being sized and proportioned to the individual foot. The arch support 14 is positioned perpendicular to the body 12 between the toe openings 18 and the tongue 20 below the medial longitudinal arch of the foot. The first end 14A and the second end 14B are sewn to the body 12 so as to provide elasticity substantially the same as that of the elastic material. Alternatively, the arch support 14 and the body 12 may be a unitary piece of elastic material as shown on FIG. 1A. Complementary patches 14C, 14D are made of synthetic materials that adhere when pressed together, commonly sold under the trademark "Velcro." Patches 14C and 14D are attached to the first end 14A and the second end 14B for securing the arch support 14 on the top of the foot.

If the footwrap is not made of ravel free material, then the borders of the body 12, arch support 14, ankle opening 16, toe openings 18, and slot 22 are finished so as to retard tearing or unraveling and to provide elasticity substantially the same as that of the elastic material.

Installation of the preferred embodiment of the footwrap is illustrated in FIGS. 2A, 2B and 2C. The footwrap 10 is installed on the foot by stepping through the ankle opening 16 and placing the toes through the toe openings 18 as shown in FIGS. 2A and 2B. The tongue 20 is then inserted into and drawn through the slot 22 until the desired compressive force is exerted along the bottom of the foot between the heel and the toes. The ends of the body are secured by meshing the "Velcro" patch 24 on the tongue 20 with the complementary "Velcro" patch 26 on the body 12 as illustrated in FIG. 2C. The arch support 14 is drawn around and over the lateral and medial sides of the foot and attached to the top of the body 12 by meshing the "Velcro" patches 14C, 14D as illustrated in FIG. 2C. The arch support 14 is cinched up as necessary to provide the desired support for the arch of the foot.

When the footwrap is in the operative position on the foot, the body 12 exerts a compressive force of predetermined magnitude along the bottom of the foot, using the heel of the foot as a fulcrum and the forefoot as a base, to relax and shorten the musculatures of the foot. The magnitude of the compressive force along the bottom of the foot can be adjusted by varying the length of tongue 20 that is inserted through the slot 22. The magnitude of this compressive force can also be adjusted by varying the elasticity of the material forming the body 12. The desired support for the arch of the foot is achieved by cinching up the arch support 14 and securing on top of the foot. The support for the arch may be adjusted by varying the length of overlap of the first end 14A and the second end 14B. The support of the arch may also be adjusted by varying the elasticity of the material forming the arch support 14.

Figure 3:
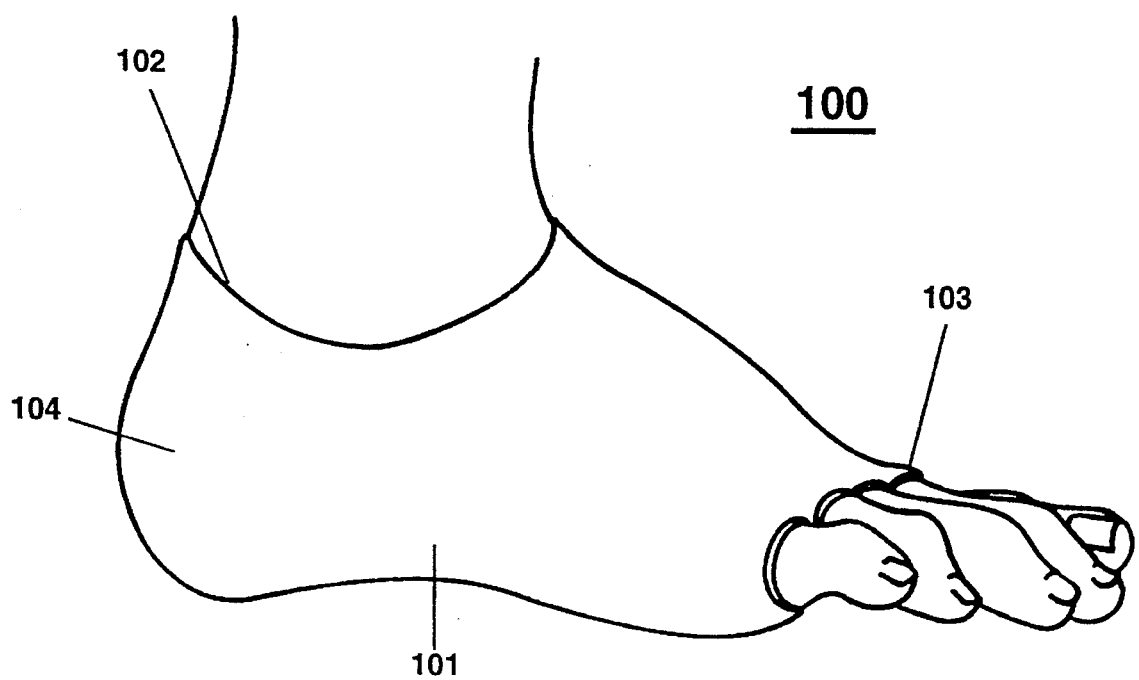
FIG. 3 shows another embodiment of the footwrap in operative position on the foot.
Figure 3A:
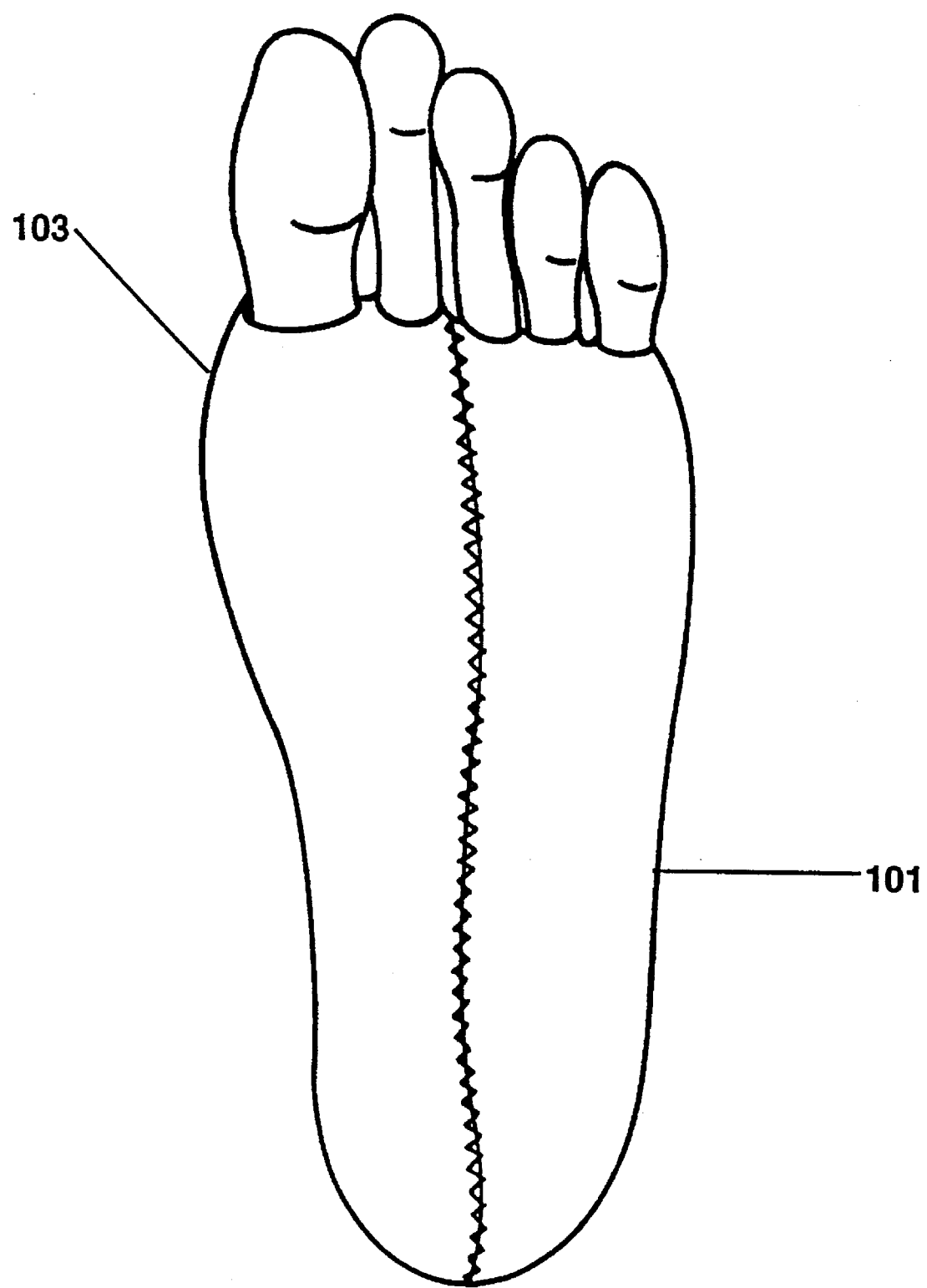
FIG. 3A shows the footwrap of FIG. 3 with a seam extending along the bottom of the foot and the rear of the heel.

The preferred embodiment of the footwrap achieves the several objects of the invention and is well suited for practical use. Other embodiments of the footwrap might be made. For instance, FIGS. 3 and 3A illustrate another embodiment of the footwrap 100 having a modified tubular body 101 made of elastic material with an ankle opening 102, toe openings 103 and a heel cup 104. The body 101 may be constructed of a unitary seamless piece of elastic material, as shown in FIG. 3, or from a sheet of elastic material folded substantially in half and joined in a seam extending along the bottom of the foot and the rear of the heel, as shown in FIG. 3A. This embodiment of the footwrap envelops the foot from the heel to the toes and exerts a predetermined compressive force to support the arch of the foot and along the bottom of the foot to shorten and relax the musculatures of the foot.

I claim:

1. An elastic footwrap for treating plantar fasciitis, which comprises:
   a) a body for covering the top and bottom of the foot, the body being made of elastic material and having a first end, a second end, an ankle opening and a plurality of toe openings;
   b) the ankle opening being positioned to extend from above the heel forward along both sides of the foot just below the ankle to the top of the foot;
   c) the toe openings being positioned forward of the ankle opening so that the toes can be inserted through the toe openings when the footwrap is installed on the foot;
   d) a means for securing the first end of the body and the second end of the body so that a predetermined compressive force is exerted along the bottom of the foot;
   e) an arch support for enveloping and supporting the arch of the foot, the arch support being made of elastic material and having a first end and a second end;
   f) the arch support being positioned perpendicular to the body; and
   g) a means for securing the first end of the arch support and the second end of the arch support so that the arch support envelops and supports the arch of the foot.

2. The footwrap of claim 1, wherein the body and the arch support are a unitary piece of elastic material.

3. The footwrap of claim 1, wherein the body and the arch support are separate pieces of elastic material.

4. The footwrap of claim 1, wherein the means for securing the first end of the arch support and the second end of the arch support comprises complementary patches of synthetic materials that adhere when pressed together, disposed on the first end of the arch support and the second end of the arch support.

5. An elastic footwrap for treating plantar fasciitis, which comprises:
   a) a body for covering the top and bottom of the foot, the body being made of elastic material and having a first end, a second end, an ankle opening and a plurality of toe openings;
   b) the ankle opening being positioned to extend from above the heel forward along both sides of the foot just below the ankle to the top of the foot;
   c) the toe openings being positioned forward of the ankle opening so that the toes can be inserted through the toe openings when the footwrap is installed on the foot;
   d) a means for securing the first end of the body and the second end of the body so that a predetermined compressive force is exerted along the bottom of the foot, comprising a slot disposed within the second end of the body, a tongue positioned at and formed by the first end of the body, the tongue being inserted through the slot, and a fastener means to secure the tongue through the slot;
   e) an arch support for enveloping and supporting the arch of the foot, the arch support being made of elastic material and having a first end and a second end;
   the arch support being positioned perpendicular to the body; and
   g) a means for securing the first end of the arch support and the second end of the arch support so that the arch support envelopes and supports the arch of the foot.

6. The footwrap of claim 3, wherein the arch support is attached to the body.

7. The footwrap of claim 5, wherein the fastener means comprises complementary patches of synthetic materials that adhere when pressed together, the patches being located on the tongue and on a part of the body located immediately adjacent to the tongue.

* * * * *